US009820978B2

(12) United States Patent
Cohen et al.

(10) Patent No.: US 9,820,978 B2
(45) Date of Patent: Nov. 21, 2017

(54) TREATMENT OF CEREBRAL ISCHEMIA

(75) Inventors: Daniel Cohen, Le Vesinet (FR); Ilya Chumakov, Vaux le Penil (FR); Serguei Nabirochkin, Chatenay Malabry (FR); Emmanuel Vial, Paris (FR); Mickaël Guedj, Paris (FR)

(73) Assignee: PHARNEXT, Issy les Moulineaux (FR)

( * ) Notice: Subject to any disclaimer, the term of this patent is extended or adjusted under 35 U.S.C. 154(b) by 54 days.

(21) Appl. No.: 14/002,429

(22) PCT Filed: Mar. 1, 2012

(86) PCT No.: PCT/EP2012/053568
§ 371 (c)(1),
(2), (4) Date: Dec. 3, 2013

(87) PCT Pub. No.: WO2012/117075
PCT Pub. Date: Sep. 7, 2012

(65) Prior Publication Data
US 2014/0080873 A1    Mar. 20, 2014

Related U.S. Application Data

(60) Provisional application No. 61/468,658, filed on Mar. 29, 2011, provisional application No. 61/493,606, filed on Jun. 6, 2011.

(30) Foreign Application Priority Data

Mar. 1, 2011  (EP) ..................................... 11305217
Jun. 6, 2011  (EP) ..................................... 11305687

(51) Int. Cl.
| | |
|---|---|
| *A61K 31/197* | (2006.01) |
| *A61K 31/185* | (2006.01) |
| *A61K 31/64* | (2006.01) |
| *A61K 31/138* | (2006.01) |
| *A61K 31/137* | (2006.01) |
| *A61K 31/42* | (2006.01) |
| *A61P 9/10* | (2006.01) |
| *A61K 31/44* | (2006.01) |
| *A61K 31/195* | (2006.01) |
| *A61K 31/445* | (2006.01) |
| *A61K 45/06* | (2006.01) |
| *A61K 31/145* | (2006.01) |
| *A61K 31/164* | (2006.01) |
| *A61K 31/428* | (2006.01) |

(52) U.S. Cl.
CPC ............ *A61K 31/44* (2013.01); *A61K 31/137* (2013.01); *A61K 31/138* (2013.01); *A61K 31/145* (2013.01); *A61K 31/164* (2013.01); *A61K 31/185* (2013.01); *A61K 31/195* (2013.01); *A61K 31/197* (2013.01); *A61K 31/42* (2013.01); *A61K 31/428* (2013.01); *A61K 31/445* (2013.01); *A61K 31/64* (2013.01); *A61K 45/06* (2013.01)

(58) Field of Classification Search
CPC .... A61K 31/197; A61K 31/185; A61K 31/64; A61K 31/138; A61K 31/137; A61K 31/42
See application file for complete search history.

(56) References Cited

U.S. PATENT DOCUMENTS

| | | |
|---|---|---|
| 6,391,922 B1 | 5/2002 | Fogel |
| 8,716,269 B2 | 5/2014 | Cohen et al. |
| 8,741,886 B2 | 6/2014 | Cohen et al. |
| 8,809,302 B2 | 8/2014 | Cohen et al. |
| 8,865,769 B2 | 10/2014 | Cohen et al. |
| 9,144,558 B2 | 9/2015 | Cohen et al. |
| 9,241,933 B2 | 1/2016 | Cohen et al. |
| 9,248,111 B2 | 2/2016 | Cohen et al. |
| 9,636,316 B2 | 5/2017 | Cohen et al. |
| 2012/0088744 A1 | 4/2012 | Cohen et al. |
| 2013/0090307 A1 | 4/2013 | Cohen et al. |
| 2014/0038927 A1 | 2/2014 | Cohen etal. |
| 2014/0178463 A1 | 6/2014 | Cohen et al. |
| 2014/0235599 A1 | 8/2014 | Cohen et al. |
| 2014/0357648 A1 | 12/2014 | Cohen et al. |
| 2014/0371229 A1 | 12/2014 | Cohen et al. |
| 2014/0371277 A1 | 12/2014 | Cohen et al. |
| 2014/0378440 A1 | 12/2014 | Cohen et al. |
| 2016/0000736 A1 | 1/2016 | Cohen et al. |
| 2016/0136143 A1 | 5/2016 | Cohen et al. |
| 2016/0193163 A1 | 7/2016 | Cohen et al. |
| 2016/0206603 A1 | 7/2016 | Cohen et al. |

FOREIGN PATENT DOCUMENTS

WO    WO 2012/117073    9/2012

OTHER PUBLICATIONS

Definition of prevent, Princeton University "About WordNet." WordNet. Princeton University. 2010. <http://wordnet.princeton.edu>, accessed Sep. 18, 2012.*
Aksenova et al. Current Neurovascular Research 2005, 2, 73-89.*
Davies J. Psychiatry Neurosci 2003, 28 (4), 263-274.*
Tuttolomondo, A. et al. "Neuron Protection as a Therapeutic Target in Acute Ischemic Stroke" *Current Topics in Medicinal Chemistry*, Oct. 2009, pp. 1317-1334, vol. 9, No. 14.
O'Collins, V. E. et al. "Evaluation of combination therapy in animal models of cerebral ischemia" *Journal of Cerebral Blood Flow & Metabolism*, Feb. 1, 2012, pp. 585-597, vol. 32, No. 4.
Costa, C. et al. "Coactivation of $GABA_A$ and $GABA_B$ Receptor Results in Neuroprotection During In Vitro Ischemia" *Stroke*, Feb. 2004, pp. 596-600, vol. 35.
Zhou, C. et al. "Neuroprotection of γ-Aminobutyric Acid Receptor Agonists Via Enhancing Neuronal Nitric Oxide Synthase (Ser847) Phosphorylation Through Increased Neuronal Nitric Oxide Synthase and PSD95 Interaction and Inhibited Protein Phosphatase Activity in Cerebral Ischemia" *Journal of Neuroscience Research*, Oct. 2008, pp. 2973-2983, vol. 86, No. 13.
Engelhard, K. et al. "Der neuroprotektive Einfluss des Glutamat-Antagonisten Acamprosat nach experimenteller zerebraler Ischamie" *Der Anaesthesist*, Sep. 2000, pp. 816-821, vol. 49, No. 9.

(Continued)

*Primary Examiner* — Irina Neagu
(74) *Attorney, Agent, or Firm* — Saliwanchik, Lloyd & Eisenschenk (57) ABSTRACT

The present invention relates to new compositions and methods for protecting neuronal cells from ischemic or hypoxic events. More precisely, this invention provides new combinatorial therapies that efficiently protect neuronal cells from ischemia or hypoxia.

18 Claims, 3 Drawing Sheets

(56) References Cited

OTHER PUBLICATIONS

Baudelet, C. et al. "Evidence for a Neuroprotective Effect of Pyrid-3-yl-sulphonyl-urea in Photochemically Induced Focal Ischaemia in Rats: Magnetic Resonance Imaging Evaluation" *J. Pharm. Pharmacol.*, Aug. 8, 1999, pp. 967-960, vol. 51, No. 8.
Nagai, H. et al. "The effect of a novel loop diuretic, torasemide, on ischemic cerebral edema in Mongolian gerbils" *Japanese Journal of Pharmacology*, Jan. 1, 1992, p. 289P, vol. 59, No. Suppl. 1, abstract P-130.
Staub, F. et al. "Swelling of glial cells in lactacidosis and by glutamate: significance of $Cl^-$-transport" *Brain Research*, Apr. 30, 1993, pp. 69-74, vol. 610, No. 1.
Nistico, R. et al. "The blockade of $K^+$-ATP channels has neuroprotective effects in an in vitro model of brain ischemia" *International Review of Neurobiology*, Jan. 1, 2007, pp. 383-395, vol. 82.
Westermaier, T. et al. "The authors reply" *Critical Care Medicine*, Oct. 1, 2010, pp. 2084-2085, vol. 38, No. 10.
Written Opinion in International Application No. PCT/EP2012/053568, dated Sep. 10, 2012, pp. 1-13.
Reilly, M. et al. "Effects of Acamprosate on Neuronal Receptors and Ion Channels Expressed in *Xenopus* Oocytes" Alcoholism: Clinical and Experimental Research, Feb. 2008, pp. 188-196, vol. 32. No. 2.
Bliss, C. I. "The Toxicity of Poisons Applied Jointly" Annals of Applied Biology, 1939, pp. 585-615.

\* cited by examiner

TREATMENT OF CEREBRAL ISCHEMIA

FIELD OF THE INVENTION

The present invention relates to the field of medicine. It provides new compositions and methods for treating or protecting individuals in need thereof from cerebral ischemia or hypoxia. The invention also relates to new compositions and methods for treating stroke. More specifically, the invention relates to novel methods and drug combinations to protect neuronal cells from ischemia- or hypoxia-induced cell death. The compositions and methods of the invention may be used to treat brain ischemic or hypoxic injuries in any mammalian subject.

BACKGROUND OF THE INVENTION

Ischemia is a condition in which there is insufficient blood flow to a given part of the body to meet metabolic demand. This shortage of oxygen, glucose and other nutrients leads to tissue damage at the ischemic area. It can affect an entire organ, a limb or just a tissue part, depending of the vascular system involved. There are various types of ischemia with specific mechanisms, depending on the area experiencing the ischemic insult, but they all share overall processes responsible for such an insult with globally common consequences.

Many events can lead to an insufficient blood supply to a given tissue: atherosclerosis, thromboembolism, hypoglycemia, tachycardia, hypotension, outside compression of a blood vessel (e.g. by a tumor or following a trauma), embolism, sickle cell disease, localized extreme cold, tourniquet application, arteriovenous malformations, peripheral artery occlusive disease, hemorrhage.

One major consequence of ischemia is the lack of oxygen normally supplied through binding to hemoglobin in red blood cells. The affected tissue rapidly becomes hypoxic if not anoxic. This, added to the lack of glucose, the energy supply, leads to the release of proteolytic enzymes, reactive oxygen species and inflammatory mediators. This so-called ischemic cascade will ultimately cause cell death and tissue damage. Ischemia can thus develop in any part of the body, such as a limb, intestine, heart or brain. The heart and brain are among the organs that are the most quickly damaged by ischemia: necrosis becomes irreversible after only about 3-4 minutes after onset.

Cerebral ischemia is ischemia of the brain tissues resulting in loss of brain cells. Unlike other tissues which can survive extended periods of hypoxia, brain tissue is particularly sensitive to deprivation of oxygen or energy. Permanent damage to neurons can occur even during very brief periods of hypoxia or ischemia. At present, there is no effective neuroprotective strategy for the treatment of cerebral ischemia or hypoxia. Cerebrovascular disease is the third most common cause of death worldwide (WHO 2008), being responsible for 10.8% of worldwide deaths. In addition, it is one of the first causes of long-term disability in Western countries, with more than 50% of patients being left with a motor disability and a significant loss of quality-adjusted life years (QALY). The risk of cerebral ischemia increasing with age, the burden of cerebral ischemia is becoming greater as the population is aging. The improvement of health care by the development of faster and more effective therapy would therefore have an important medical and socioeconomic impact worldwide and is greatly needed.

Symptoms of cerebral ischemia and their severity vary greatly depending on the cerebral region(s) affected. For instance, they may include weakness in one entire side of the body, impairments in speech or vision and/or mental confusion. Focal cerebral ischemia, which occurs when a blood clot has occluded a cerebral vessel and is confined to a specific region of the brain, is usually caused by thrombosis or embolism. Global cerebral ischemia, which occurs when blood flow to the entire brain is stopped or drastically reduced, is commonly caused by cardiovascular disease. The area(s) of brain tissue affected as well as the delay in diagnosis and treatment are essential factors determining the outcome of cerebral ischemia, i.e., survival and level of disability after recovery.

One major consequence of cerebral ischemia is neuronal damage, which is mediated by the ischemic cascade that results in tissue damage leading to subsequent neuronal death and to disruption of the blood-brain barrier. It is estimated that 2 million brain cells die every minute after ischemic stroke onset. In addition, restoration of blood flow after a period of ischemia can actually be more damaging than the ischemia itself. The so-called reperfusion injury can result in acceleration of neuronal death.

There is, currently, no effective drug therapy to help patients during the acute phase of brain ischemia except thrombolysis and new endovascular devices or techniques which only a limited number of patients will benefit from. This is due to one major issue: a very narrow therapeutic window of less than 6 h from ischemia onset. Another major issue is the invasiveness and complexity of these procedures.

New therapies are currently contemplated which aim at (i) regenerating damaged brain areas to regain neurological function and (ii) targeting the ischemic cascade to minimize and even prevent brain damage. Unfortunately, so far, these new therapies have been effective in experimental settings but have failed translation to clinical practice.

Stimulation of neurogenesis using endogenous repair mechanisms such as neuronal progenitor cells or transplantation of stem cells is being actively investigated. Unfortunately, issues such as survival of the cells, proper differentiation and proper connectivity of the new neuronal cells remain unsolved so far (1).

Antioxidant enzymes, primarily superoxide dismutase (SOD), in association with catalase, and glutathione peroxidase, have been tested in vivo but showed no improvement in cerebral blood flow or neurological recovery (2).

Newer therapeutic approaches with different modes of action and a wider therapeutic window are currently being investigated for ischemic stroke: glutamate antagonists, anti-inflammatory agents, anti-apoptotic agents, and ion-channel modulators.

Glutamate is the most abundant excitatory neurotransmitter in the mammalian nervous system. It activates glutamate receptors that are classified into three ionotropic classes (NMDA, AMPA and kainate receptors) and three metabotropic classes. Under normal conditions, glutamate concentration is maintained by glial and neuronal systems. During ischemia, an abnormally high concentration of extracellular glutamate is observed in the brain. Excessive accumulation of glutamate in synaptic clefts leads to the overactivation of glutamate receptors that results in pathological processes and finally in neuronal cell death. This process, named excitotoxicity, is commonly observed in neuronal tissues under ischemic conditions. From glutamate receptor over-activation ensues an accumulation in postsynaptic cells of several ion species, especially calcium (28). Overload of calcium is a key process of excitotoxicity. It results in deleterious cellular processes especially when specific structures such as mitochondria or endoplasmic reticula are no longer able to sequester cytoplasmic calcium. Excessive calcium overload in mitochondria is associated with the increased generation of reactive oxygen species as well as the release of proapoptotic mitochondrial proteins, which are both deleterious (28,29). Transient or sustained calcium influx into cells also activates a number of deleterious enzymes, including nitric oxide synthase, phospholipases, endonucleases, and proteases such as caspases and calpain (30).

Several glutamate receptor antagonists have been tested to counteract excitotoxicity. However, effects of glutamate receptor antagonists, such as the NMDA receptor antagonists Selfotel, Eliprodil and Aptiganel (Cerestat), could not be validated in clinical studies and several studies have been stopped (3). Dizolcipine (MK801), another NMDA receptor antagonist, is associated with numerous side effects. Calcium channel blockers such as Nimodipine and Flunarizine also showed no significant benefit versus placebo in clinical trials (4). A phase III trial with the AMPA receptor antagonist YM872 (zonampanel) is ongoing and seeks to determine its potential efficacy in combination with tPA thrombolysis.

A variety of anti-inflammatory drugs have been shown to reduce ischemic damage in animal studies. Commonly used anti-inflammatory agents are aspirin and the lipid-lowering statins. In addition, two leukocyte adhesion inhibitors, Enlimomab and LeukArrest, were studied in patients with ischemic stroke but secondary effects seemed to be greater than their therapeutic effects (5).

Ion channel modulators (i.e., Nimodipine, Fosphenytoin, Maxipost) failed at phase III due to a lack of demonstrated benefit (6).

Anti-apoptotic agents such as caspase inhibitors have been shown to reduce the area of ischemic damage in rodent stroke models (7). However, a recent study with erythropoietin yielded negative effects and raised safety concerns with an increased risk of death and further cerebrovascular events (8).

Due to the above-mentioned societal impact of cerebral ischemia, there is still a need for drugs effective in protecting neuronal cells during an ischemic or hypoxic event, following its onset, or in a preventive way in a patient at risk.

SUMMARY OF THE INVENTION

The present invention provides novel compositions and methods for treating brain ischemia and hypoxia. More specifically, the present invention stems from the discovery of specific drug combinations that provide remarkable neuroprotective effects against ischemia or hypoxia and therefore represent novel treatments for such conditions.

The invention thus discloses novel therapies for the treatment of brain ischemic or hypoxic injuries caused by various pathological conditions resulting in reduced blood flow or in reduced oxygen content.

An object of the invention relates more specifically to a composition comprising:
Baclofen and Acamprosate,
Baclofen and Torasemide,
Baclofen and Torasemide and Acamprosate,
Mexiletine and Cinacalcet, or
Sulfisoxazole and Torasemide,
or any of their pharmaceutically acceptable salts, enantiomers, racemates, prodrugs, derivatives or metabolites, for use in the treatment of a brain ischemic or hypoxic injury.

The treatment may be preventive, particularly in subjects at risk, or curative, and may be used to treat focal or global ischemic injuries, as well as hypoxic injuries, of different origins. It is particularly suited to treat ischemia or hypoxia in subjects suffering from, having suffered from, or susceptible to suffer from, e.g., stroke, acute ischemic stroke, transient ischemic attack, acute hemorrhagic stroke, head trauma, brain hemorrhages, cardiac arrest, cerebral edema, hydrocephalus, asphyxia, thrombosis, embolism, thromboembolism, atherosclerosis, prolonged severe hypotension, intrauterine hypoxia, birth hypoxia, cardiac surgery complications or neurosurgery complications.

Another object of the invention relates to a composition as described above, for use to reduce, prevent or retard ischemia- or hypoxia-induced neuronal damage or neuronal cell death.

Another object of the invention relates to a composition as described above, for use to protect a subject from brain ischemia or hypoxia.

The present invention also relates to a composition comprising:
Baclofen and Acamprosate,
Baclofen and Torasemide,
Baclofen and Torasemide and Acamprosate,
Mexiletine and Cinacalcet, or
Sulfisoxazole and Torasemide,
or any of their pharmaceutically acceptable salts, enantiomers, racemates, prodrugs, derivatives or metabolites, for use in the curative or preventive treatment of stroke in a subject.

The invention also relates to a composition as described above, for use to reduce, prevent or retard stroke-induced neuronal damage or neuronal cell death.

The invention also relates to pharmaceutical compositions per se comprising at least one drug combination as disclosed above. The pharmaceutical compositions of the invention typically comprise one or several pharmaceutically acceptable excipient(s) or carrier(s). As will be further disclosed in the present application, the compounds in a combinatorial therapy according to the invention may be formulated or administered to the subject together, separately or sequentially, possibly through different routes and protocols. In a preferred embodiment, the compositions of the invention are administered repeatedly to the subject.

The invention also relates to methods of treating brain ischemia or hypoxia in a subject in need thereof, the method comprising simultaneously, separately or sequentially administering to said subject a drug combination or a composition as disclosed above.

The present invention also relates to methods of treating stroke in a subject in need thereof, the method comprising simultaneously, separately or sequentially administering to said subject a drug combination or a composition as disclosed above.

A further object of this invention relates to the use of the above-described drug combinations or compositions for the manufacture of a medicament for the treatment of brain ischemia or hypoxia.

A further object of this invention relates to the use of the above-described drug combinations or compositions for the manufacture of a medicament for the treatment of stroke.

The treatment according to the invention may be used alone or in combination or in alternation with other therapies of such conditions. The invention is applicable to any mammalian, particularly human subject.

DETAILED DESCRIPTION OF THE INVENTION

The present invention provides new therapeutic approaches for treating brain ischemic or hypoxic injuries. The invention discloses specific drug combinations and methods allowing effective protection of neuronal cells against ischemia or hypoxia.

Within the context of the present invention, the terms brain "ischemia" or "ischemic injury" refer to a condition occurring in subjects having insufficient blood supply to the brain or a region of the brain. More specifically, the term ischemia or ischemic injury refers to any pathological state of the brain or a region thereof in which cerebral blood flow is insufficient to meet the metabolic demands of cerebral tissue, resulting in damage to the entire brain or wide areas of the brain (global ischemia) or to a specific region of the brain (focal ischemia).

The terms brain "hypoxia" or "hypoxic injury" refer to a condition occurring in subjects having reduced oxygen supply to the brain or a region of the brain. Hypoxia may result from ischemic events. However, hypoxia may also occur without ischemia, when the oxygen content in blood vessels decreases without diminution of blood flow. Hypoxia according to the invention also comprises anoxia which is a complete tissue deprivation of oxygen supply.

The term "brain ischemic" or "brain hypoxic injury" therefore particularly includes a brain injury in which neuronal cells are damaged, or subjected to cell death, as a result of reduced blood flow (ischemia) or as a result of reduced oxygen content (hypoxia).

Ischemia and hypoxia may occur in subjects under different situations, such as under conditions of stroke, acute ischemic stroke, transient ischemic attack, acute hemorrhagic stroke, head trauma, brain hemorrhages, cardiac arrest, cerebral edema, hydrocephalus, asphyxia, vaso-occlusive conditions, embolism, thrombosis, thromboembolism, atherosclerosis, prolonged severe hypotension, intrauterine hypoxia, birth hypoxia, cardiac surgery complications or neurosurgery complications.

As used herein, the term "treatment" includes the curative treatment or the preventive treatment of brain ischemic or hypoxic injuries.

A curative treatment is used once ischemia or hypoxia is induced in a subject. The treatment is then typically used to reduce neuronal damage or neuronal cell death in subjects suffering from ischemia or hypoxia. The curative treatment also includes health improvement and recovery of patients having experienced pathological conditions resulting in reduced blood flow or in reduced oxygen content, as described above, by limiting neuronal cell death and brain damage in these subjects. The curative treatment also includes the diminution of secondary ischemic injuries such as reperfusion injuries. A curative acute treatment is preferably started as early as possible upon detection of ischemia or hypoxia, more preferably within hours.

The preventive treatment may be used in subjects at risk of suffering from cerebral ischemia or hypoxia, in order to prevent, lessen or retard neurological insults caused by ischemia or hypoxia. The preventive treatment includes a protection of neuronal cells from damage or death in conditions of glucose and oxygen deprivation as well as in conditions of glutamate excitotoxicity. Subjects at risk include subjects susceptible to suffering from, or who have already suffered from, stroke, acute ischemic stroke, transient ischemic attack, acute hemorrhagic stroke, head trauma, brain hemorrhages, cardiac arrest, cerebral edema, hydrocephalus, asphyxia, vaso-occlusive conditions, embolism, thromboembolism, atherosclerosis, or prolonged severe hypotension. It is well known that patients having suffered from many of the above conditions are likely to relapse. Consequently, the herein-documented protective effect of compound combinations of the invention can be used as an efficient preventive therapy in such patients at risk. The subjects at risk also include subjects who undergo or who will undergo cardiac surgery or neurosurgery. Furthermore, the preventive therapy of the invention can also be used for other patients with elevated risk factors for developing cerebral ischemia or hypoxia, in relation to hypertension, cigarette smoking, physical inactivity, obesity, cardiovascular disease, high levels of total cholesterol, and atrial fibrillation. Pregnant women are also at increased risk during pregnancy and the postpartum period if they develop cardiovascular conditions such as preeclampsia.

The term "combination" designates a treatment wherein at least two drugs are co-administered to a subject to cause a biological effect. In a combined therapy or composition according to this invention, the at least two drugs may be administered together or separately, at the same time or sequentially. Also, the at least two drugs may be administered through different routes and protocols. As a result, although they may be formulated together, the drugs of a combination may also be formulated separately.

The term "salt" refers to a pharmaceutically acceptable and relatively non-toxic, inorganic or organic acid addition salt of a compound of the present invention. Pharmaceutical salt formation typically consists of pairing an acidic, basic or zwitterionic drug molecule with a counterion to create a salt version of the drug. A wide variety of chemical species can be used in neutralization reactions. Though most salts of a given active principle are bioequivalents, some may have, among others, increased solubility or bioavailability properties. Salt selection is now a common standard operation in the process of drug development as taught by H. Stahl and C. G. Wermuth in their handbook (24). Pharmaceutically acceptable salts of the invention thus include those obtained by reacting the main compound, functioning as a base, with an inorganic or organic acid to form a salt, for example, salts of acetic acid, nitric acid, tartaric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts.

The term "prodrug" as used herein refers to any derivative (or precursor) of a compound which, when administered to a biological system (e.g., a human organism), generates said compound as a result of, e.g., spontaneous chemical reaction(s), enzyme-catalyzed chemical reaction(s), and/or metabolic chemical reaction(s). Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Specific technical guidance for the selection of suitable prodrugs is general common knowledge (9-13). Furthermore, the preparation of prodrugs may be performed by conventional methods known by those skilled in the art. Methods which can be used to synthesize prodrugs are described in numerous reviews on the subject (12; 14-20). For example, Arbaclofen Placarbil is listed in the ChemID plus Advance database and Arbaclofen Placarbil is a well-known prodrug of Baclofen (21).

The term "metabolite" of a drug as used herein refers to a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, preferably that has a protective activity against ischemia- or hypoxia-induced neuronal cell death. Examples of metabolites include hydroxylated forms of Torasemide resulting from the hepatic metabolism of the drug (DrugBank database (25)).

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compounds having lost one or more substituent as listed above. For example, Homotaurine is a deacetylated derivative of Acamprosate. Preferred derivatives of a compound are molecules having a substantial degree of similarity to said compound, as determined by known methods. Similar compounds along with their index of similarity to a parent molecule can be found in numerous databases such as PubChem (see Worldwide Website: pubchem.ncbi.nlm.nih.gov/search/) or DrugBank (see WorldWide Website: drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector (31-32) available online (see Worldwide Website: ebi.ac.uk/thornton-srv/software/SMSD/). Preferred derivatives should be both structurally and functionally related to a parent compound, i.e., they should also retain at least part of the activity of the parent drug, more preferably they should have a protective activity against ischemia- or hypoxia-induced neuronal cell death.

In a preferred embodiment, the designation of a compound or drug is meant to designate the compound per se, as well as any pharmaceutically acceptable salt, prodrug, metabolite, derivative, hydrate, isomer, or racemate thereof, of any chemical purity.

In a particular embodiment, a sustained-release formulation of the compound is used.

As discussed above, the invention relates to particular drug combinations which allow an effective protection of neuronal cells from ischemia or hypoxia in individuals in need thereof. More specifically, the invention discloses compositions comprising various combinations of Baclofen, Acamprosate, Torasemide, Mexiletine, Cinacalcet or Sulfisoxazole, which provide significant protection of neuronal cells against ischemia or hypoxia.

Table 1 below provides the CAS number for each of these compounds as well as a non limitative list of examples of salts, racemates, prodrugs, metabolites or derivatives for these compounds suitable for use in the compositions of the invention.

TABLE 1

| Drug | CAS Numbers | Class or Tanimoto similarity index |
|---|---|---|
| Acamprosate and related compounds | | |
| Acamprosate | 77337-76-9; 77337-73-6 | |
| Homotaurine | 3687-18-1 | 0.73 |
| Ethyl Dimethyl Ammonio Propane Sulfonate | / | 0.77 |
| Taurine | 107-35-7 | 0.5 |
| Baclofen and related compounds | | |
| Baclofen | 1134-47-0; 66514-99-6; 69308-37-8; 70206-22-3; 63701-56-4; 63701-55-3 | |
| 3-(p-chlorophenyl)-4-hydroxybutyric acid | / | Metabolite |
| Arbaclofen placarbil | 847353-30-4 | Prodrug |
| Mexiletine and related compounds | | |
| Mexiletine | 31828-71-4; 5370-01-4 | |
| 6-Hydroxymethylmexiletine | 53566-98-6 | Metabolite |
| 4-Hydroxymexiletine | 53566-99-7 | Metabolite |
| 3-Hydroxymexiletine (MHM) | 129417-37-4 | Metabolite |
| N-Hydroxymexiletine glucuronide | 151636-18-9 | Metabolite |
| Sulfisoxazole and related compounds | | |
| Sulfisoxazole | 127-69-5; 4299-60-9 | |
| N(4)-Acetylsulfisoxazole | 4206-74-0 | Metabolite |
| Sulfisoxazole acetyl | 80-74-0 | Prodrug |
| Sulfamethoxazole | 723-46-6 | 0.52 |
| Cinacalcet and related compounds | | |
| Cinacalcet | 226256-56-0; 364782-34-3 | |
| Hydrocinnamic acid | 501-52-0 | Metabolite |

TABLE 1-continued

| Drug | CAS Numbers | Class or Tanimoto similarity index |
|---|---|---|
| Torasemide and related compounds | | |
| Torasemide | 56211-40-6; 72810-59-4 | |
| Hydroxytorasemide | 99300-68-2; 99300-67-1 | Metabolites |
| Carboxytorsemide | / | Metabolite |
| Tolbutamide | 64-77-7 | 0.55 |

Specific examples of Baclofen prodrugs are given in Hanafi et al. (2011) (26) who show Baclofen esters and ester carbamates to be of particular interest for CNS targeting. Hence such prodrugs are particularly suitable for compositions of this invention. Baclofen placarbil as mentioned before is also a well-known prodrug and may thus be used instead of Baclofen in compositions of the invention. Other prodrugs for Baclofen can be found in the following patent applications: WO2010102071, US2009197958, WO2009096985, WO2009061934, WO2008086492, US2009216037, WO2005066122, US2011021571, WO2003077902 and WO2010120370.

Useful prodrugs for Acamprosate such as pantoic acid esters, neopentyl sulfonyl esters, neopentyl sulfonyl ester prodrugs or masked carboxylate neopentyl sulfonyl ester prodrugs of Acamprosate are notably listed in WO2009033069, WO2009033061, WO2009033054, WO2009052191, WO2009033079, US 2009/0099253, US 2009/0069419, US 2009/0082464, US 2009/0082440, and US 2009/0076147.

As mentioned before, Homotaurine can be used instead of Acamprosate in compositions of this invention.

As disclosed in the examples, the inventors have found that combinatorial treatments comprising at least:

Baclofen and Acamprosate,
Baclofen and Torasemide,
Baclofen and Torasemide and Acamprosate,
Mexiletine and Cinacalcet, or
Sulfisoxazole and Torasemide, have a strong protective effect on neuronal cells in conditions of glucose and oxygen deprivation in a model of ischemia/hypoxia. The results further show that these combinatorial treatments also effectively protect neurons against glutamate toxicity. The results show an unexpected synergistic effect of the combined drugs.

The present invention therefore provides a novel treatment of ischemia or hypoxia, in particular a novel treatment for protecting neuronal cells from ischemia or hypoxia, with a composition comprising any one of the following combinations:

Baclofen and Acamprosate,
Baclofen and Torasemide,
Baclofen and Torasemide and Acamprosate,
Mexiletine and Cinacalcet, or
Sulfisoxazole and Torasemide.

Thus, one embodiment of the invention is the use of any one the above combinations of drugs, or their pharmaceutically acceptable salts, enantiomers, racemates, prodrugs, derivatives or metabolites, for protecting neuronal cells from ischemia or hypoxia in a subject in need thereof.

In a particular embodiment, the invention relates to the use of the above-mentioned combinations of drugs, or their pharmaceutically acceptable salts, enantiomers, racemates, prodrugs, derivatives or metabolites, for preventing, lessening or retarding neuronal cell death in a subject having a brain ischemia or hypoxia.

Another embodiment of this invention relates to the use of any of the above combinations of drugs, or their pharmaceutically acceptable salts, enantiomers, racemates, prodrugs, derivatives or metabolites, for protecting neuronal cells from death in a subject at risk of having brain ischemia or hypoxia. As discussed before, subjects at risk include subjects having experienced before a brain ischemia or hypoxia, as well as subjects experiencing or susceptible to experiencing a condition or disease which can lead to cerebral ischemia or hypoxia.

The invention is particularly suited to treat brain ischemia or hypoxia in a subject suffering from, or having suffered from, or at risk of suffering from, stroke, shock, transient ischemic attack, cerebral edema, brain hemorrhages, hydrocephalus, trauma, intrauterine or birth hypoxia, embolus, atherosclerosis, or myocardial infarction.

The combination treatments of the invention are also effective and suitable to protect neuronal cells from ischemia or hypoxia in a subject undergoing cardiac surgery or neurosurgery. The treatment may be applied prior to, during, and/or after the surgery.

A preferred embodiment of the invention is the use of one of the above drug combinations for treating brain ischemia or hypoxia, more particularly for protecting neuronal cells in an individual having suffered from, suffering from, or at risk of suffering from, stroke.

It is well known that transient ischemic attacks (TIA) are a harbinger of the possible development of ischemic stroke, with half of strokes occurring within the first 2 days, and a stroke risk within 90 days over 50 times the normal risk.

Hence, another preferred embodiment of the invention is the use of one of the above combinations for treating brain ischemia or hypoxia, more particularly for protecting neuronal cells from ischemia or hypoxia in an individual having suffered from a transient ischemic attack. This embodiment therefore encompasses the use of the combinations of the invention in conjunction with other drugs or devices aiming at restoring blood or oxygen supply to the brain.

In a further particular embodiment, the invention also relates to the use of one of the above combinations for treating brain ischemia or hypoxia, more particularly for protecting neuronal cells from reperfusion injury in an individual in need thereof.

Another aspect of the invention relates to the use of any of the above combinations of drugs in the manufacture of a medicament for treating brain ischemia or hypoxia, more particularly for protecting neuronal cells from ischemia or hypoxia, in a subject.

In a preferred embodiment, the invention relates to the use of any of these compositions in the manufacture of a medicament for preventing, lessening or retarding neuronal death resulting from an ischemic or hypoxic condition or disease. In another preferred embodiment, the invention relates to the use of any of the compositions of the invention in the manufacture of a medicament for preventing, lessening, or retarding neuronal cell death in subjects suffering from, or at risk of suffering from, stroke.

As indicated previously, in a combination therapy of this invention, the compounds or drugs may be formulated together or separately, and administered together, separately or sequentially.

A further object of the invention is a method of treating brain ischemia or hypoxia in a subject in need thereof, the method comprising simultaneously, separately or sequentially administering to said subject an effective amount of a drug combination as disclosed above.

A further object of the invention is a method of treating, preventing, lessening or retarding ischemia- or hypoxia-induced neuronal cell death, the method comprising simultaneously, separately or sequentially administering to a subject in need thereof an effective amount of a drug combination as disclosed above.

In a preferred embodiment, the invention relates to a method of treating, preventing, lessening or retarding ischemia- or hypoxia-induced neuronal cell death in a subject in need thereof, comprising administering simultaneously, separately or sequentially to the subject an effective amount of:

Baclofen and Acamprosate,
Baclofen and Torasemide,
Baclofen and Homotaurine,
Baclofen and Torasemide and Acamprosate,
Mexiletine and Cinacalcet, or
Sulfisoxazole and Torasemide.

For use in the present invention, the drugs or compounds are usually mixed with pharmaceutically acceptable excipients or carriers.

As exemplified, the compound combinations of the invention strongly protect neuronal cells from oxygen and glucose deprivation as well as against glutamate toxicity. The combination treatment is effective at low doses, where the compounds alone have no substantial effect. The invention therefore provides an effective treatment, with reduced risks of side effects, notably during a long-term treatment.

The invention also relates to a pharmaceutical composition per se comprising:

Baclofen and Acamprosate,
Baclofen and Torasemide,
Baclofen and Torasemide and Acamprosate,
Mexiletine and Cinacalcet, or
Sulfisoxazole and Torasemide, or their pharmaceutically acceptable salts, enantiomers, racemates, prodrugs, derivatives or metabolites. The pharmaceutical compositions of the invention typically further comprise one or several pharmaceutically acceptable excipient(s) or carrier(s).

A further object of this invention is a method of preparing a pharmaceutical composition, the method comprising mixing an appropriate quantity of the above compounds in an appropriate excipient or carrier.

The compositions and methods of the invention are very effective and can be used alone, with no further active agent or treatment. Alternatively, although very effective, depending on the subject or specific condition, the combinations or compositions of the invention may comprise additional active compounds and/or may be used in conjunction or association or combination with additional drugs or treatments. Other additional therapies used in conjunction with drug(s) or drug(s) combination(s) according to the present invention may comprise one or more drug(s) or vascular device(s) currently used to reperfuse ischemic or hypoxic areas, drug(s) which aim to prevent neuronal damages or even one or more drug(s) currently evaluated in the frame of clinical trials.

Therapy according to the invention may be provided at home, the doctor's office, a clinic, a hospital's outpatient department, or a hospital, so that the doctor can observe the therapy's effects closely and make any adjustments needed.

The duration of the therapy depends on the stage of the disease being treated, age and condition of the patient, and how the patient responds to the treatment. The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recover from any unforeseen side effects. The drugs may also be formulated together such that one administration delivers all drugs.

The administration of each drug of the combination may be by any suitable means that results in a concentration of the drug that, combined with the other component, is able to prevent, retard, or impede neuronal cell death and neurological damage stemming from cerebral ischemia or hypoxia.

While it is possible for the drugs in the combination to be administered as the pure chemicals it is preferable to present them as a pharmaceutical composition, also referred to in this context as a pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number of dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as described herein, in combination with packaging material suitable for said formulation. In such a patient pack the intended use of a formulation for the combination treatment can be inferred by instructions, facilities, provisions, adaptations and/or other means to help use the formulation most suitably for the treatment. Such measures make a patient pack specifically suitable for and adapted to use for treatment with the combination of the present invention.

The drug may be contained, in any appropriate amount, in any suitable carrier substance. The drug may be present in an amount of up to 99% by weight of the total weight of the composition. The composition may be provided in a dosage form that is suitable for the oral, parenteral (e.g., intravenous, intramuscular), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastrointestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby provide a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycol and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as glyceryl monostearate or glyceryl distearate may be employed.

The solid tablet compositions may include a coating adapted to protect the composition from unwanted chemical changes (e.g., chemical degradation prior to the release of the active drug substance). The coating may be applied on the solid dosage form in a similar manner as that described in the Encyclopedia of Pharmaceutical Technology.

Drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogel, 1,3 butylene glycol, ethylene glycol methacrylate, and/or polyethylene glycol. In a controlled release matrix formulation, the matrix material may also include, e.g., hydrated methylcellulose, carnauba wax, stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting, and/or dispersing agents.

The pharmaceutical compositions according to the invention may be in a form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), or poly(2-hydroxyethyl-L-glutamnine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(orthoesters)).

Alternative Routes

Although less preferred and less convenient, other administration routes, and therefore other formulations, may be contemplated. In this regard, for rectal application, suitable dosage forms for a composition include suppositories (emulsion or suspension type) and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycol. Various additives, enhancers, or surfactants may be incorporated.

The pharmaceutical compositions may also be administered topically on the skin for percutaneous absorption in dosage forms or formulations containing conventionally non-toxic pharmaceutically acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, and penetration enhancers may be parabens, such as methyl or propyl p-hydroxybenzoate, benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help use the combination according to the invention.

Therapeutically effective amounts of the drugs in a combination of this invention include, e.g., amounts that are effective for reducing neuronal cell death, thereby halting or slowing the progression of the neurological damage or symptoms thereof once they have become clinically manifest.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Though the treatment might be limited to hours or several days after the onset of the ischemic or hypoxic event, chronic or at least periodically repeated long-term administration might be also indicated for patients with a high risk of experiencing cerebral ischemia or hypoxia.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the ischemic or hypoxic event, and the risk of potential side effects considering the general health status of the person to be treated. Additionally, pharmacogenomic (the effect of genotype on the pharmacokinetic, pharmacodynamic or efficacy profile of a therapy) information about a particular patient may affect the dosage used.

Except when responding to important ischemic or hypoxic events, where higher dosages may be required, the preferred dosages of each drug in the combination should be as low as possible, e.g., a dosage where the combination is effective while the drugs individually have no substantial activity.

One remarkable advantage of the invention is that each compound may be used at low doses in a combination therapy, while producing, in combination, a substantial clinical benefit to the patient. The combination therapy may indeed be effective at doses where the compounds individually have little or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably ¹⁄₁₀ of therapeutic doses. In particular examples, doses as low as ¹⁄₂₀, ¹⁄₃₀, ¹⁄₅₀, ¹⁄₁₀₀, or even lower of therapeutic doses are used. At such sub-therapeutic dosages, the compounds would exhibit no side effects, while the combination(s) according to the invention are fully effective in protecting neuronal cells from ischemia- or hypoxia-induced death.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Specific examples of dosages of drugs for use in the invention are provided below:
  Acamprosate between 1 and 2000 mg per day, preferably less than 1000 mg per day, more preferably less than 500 mg per day, even more preferably less than 200 mg per day, such dosages being particularly suitable for oral administration,
  Baclofen between 0.01 and 150 mg per day, preferably less than 100 mg per day, more preferably less than 50 mg per day, even more preferably less than 25 mg per day, such dosages being particularly suitable for oral administration,
  Torasemide orally from about 0.05 to 4 mg per day, preferably less than 2.5 mg per day, more preferably less than 1.5 mg per day, even more preferably less than 0.5 mg per day, such dosages being particularly suitable for oral administration,
  Sulfisoxazole orally from about 20 to 800 mg per day, preferably less than 400 mg per day, more preferably less than 200 mg per day, even more preferably less than 100 mg per day, such dosages being particularly suitable for oral administration,
  Homotaurine orally from about 1 to 20 mg per day, preferably less than 15 mg per day, more preferably less than 10 mg per day, even more preferably less than 5 mg per day, such dosages being particularly suitable for oral administration,
  Mexiletine orally from about 6 to 120 mg per day, preferably less than 90 mg per day, more preferably less than 60 mg per day, even more preferably less than 30 mg per day, such dosages being particularly suitable for oral administration,
  Cinacalcet orally from about 0.3 to 36 mg per day, preferably less than 20 mg per day, more preferably less than 10 mg per day, even more preferably less than 1 mg per day, such dosages being particularly suitable for oral administration.

When the composition comprises, as active ingredients, Baclofen and Acamprosate, the two compounds may be used in different ratios, e.g., at a molar ratio of Baclofen/Acamprosate comprised between from 0.1 to 1000, more preferably between from 10 to 800, or even more preferably from 100 to 400.

When the composition comprises, as active ingredients, Baclofen and Torasemide, the two compounds may be used in different ratios, e.g., at a molar ratio of Baclofen/Torasemide comprised preferably between from 0.1 to 1000, more preferably between from 0.5 to 500, or even more preferably from 1 to 10.

When the composition comprises, as active ingredients, Sulfisoxazole and Torasemide, the two compounds may be used in different ratios, e.g., at a molar ratio of Torasemide/Sulfisoxazole comprised preferably between from 0.1 to 1000, more preferably between from 1 to 100, or even more preferably from 30 to 80.

When the composition comprises, as active ingredients, Mexiletine and Cinacalcet, the two compounds may be used in different ratios, e.g., at a molar ratio of Cinacalcet/Mexiletine comprised preferably between from 0.1 to 1000, more preferably between from 0.5 to 500, or even more preferably from 1 to 100.

It will be understood that the amount of the drug actually administered shall be determined and adapted by a physician, in light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

Further aspects and advantages of the invention will be disclosed in the following experimental section, which serves to illustrate the invention.

EXAMPLES

Example 1: Protective Effect of Combination Treatments of the Invention Against Ischemia/Hypoxia-Induced Neuronal Cell Death Methods
Rat Neuronal Cortical Cell Preparation
  Rat cortical neurons are cultured as described by Singer et al. (27). Briefly pregnant female rats of 15 days gestation are killed by cervical dislocation (Rats Wistar) and the fetuses are removed from the uterus. The cortex is removed and placed in ice-cold medium of Leibovitz (L15) containing 2% of Penicillin 10,000 U/ml and Streptomycin 10 mg/ml and 1% of bovine serum albumin (BSA). Cortices are dissociated by trypsin for 20 min at 37° C. (0.05%). The reaction is stopped by the addition of Dulbecco's modified Eagle's medium (DMEM) containing DNaseI grade II and 10% of fetal calf serum (FCS). Cells are then mechanically dissociated by 3 serial passages through a 10 ml pipette and centrifuged at 515×g for 10 min at +4° C. The supernatant is discarded and the pellet of cells is resuspended in a defined culture medium consisting of Neurobasal supplemented with B27 (2%), L-glutamine (0.2 mM), 2% of PS solution and 10 ng/ml of BDNF. Viable cells are counted in a Neubauer cytometer using the trypan blue exclusion test. The cells are seeded at a density of 30,00 cells/well in 96-well plates (wells were pre-coated with poly-L-lysine (10 µg/ml)) and are cultured at +37° C. in a humidified air (95%)/CO2 (5%) atmosphere.

Oxygen and Glucose Deprivation Assays (In Vitro Model of Ischemia)

The neuroprotective effect of compounds is assessed by quantification of the neurite network (Neurofilament immunostaining (NF)) using MAP2 antibody. Riluzole, a neuroprotective drug, (RILUTECK, 5 µM) is used as positive control.

After 10 days of neuron culture, candidate drugs are solved in culture medium (+0.1% DMSO) and then pre-incubated with neurons for 1 hour before the oxygen and glucose deprivation. One hour after candidate drug incubation, the medium is removed and fresh medium without glucose is added. This medium is composed of DMEM without glucose (Invitrogen) supplemented with 2% B27, 0.2 mM L-glutamine, 1% PS solution, and 10 ng/ml of BDNF. The cells are transferred into an anaerobic incubator with 95% $N_2$ and 5% $CO_2$ at 37° C.

After 2 hours, 25 mM of D-Glucose will be added to the culture medium and cells are transferred to a classic incubator with 95% air/5% $CO_2$ at 37° C. After 24 hours of oxygen glucose reperfusion, cells are fixed by a cold solution of alcohol/acetic acid during 5 minutes.

After permeabilization with saponin (Sigma), cells are blocked for 2 hours with PBS containing 10% goat serum, then the cells are incubated with mouse monoclonal primary antibody against MAP2 (MAP2, Sigma). These antibodies are revealed with Alexa Fluor 488 goat anti-mouse IgG (Molecular probe).

Nuclei of cells are labelled by a fluorescent marker (Hoechst solution, SIGMA). Six wells per condition are used to assess neuronal survival in 3 different cultures.

For each condition 2×10 pictures per well are taken and analyzed using InCell Analyzer™ 1000 (GE Healthcare) with 20× magnification.

Results

As shown in Table 2 below, all of the claimed drug combinations give a protective effect against ischemia/hypoxia-induced cell death for cortical neuronal cells.

TABLE 2

| Drug Combination | Protective effect against ischemia/hypoxia |
| --- | --- |
| Baclofen-Acamprosate | + |
| Baclofen-Torasemide | + |
| Baclofen-Homotaurine | + |

TABLE 2-continued

| Drug Combination | Protective effect against ischemia/hypoxia |
| --- | --- |
| Baclofen-Acamprosate-Torasemide | + |
| Mexiletine and Cinacalcet | + |
| Sulfisoxazole and Torasemide | + |

Figure 1:
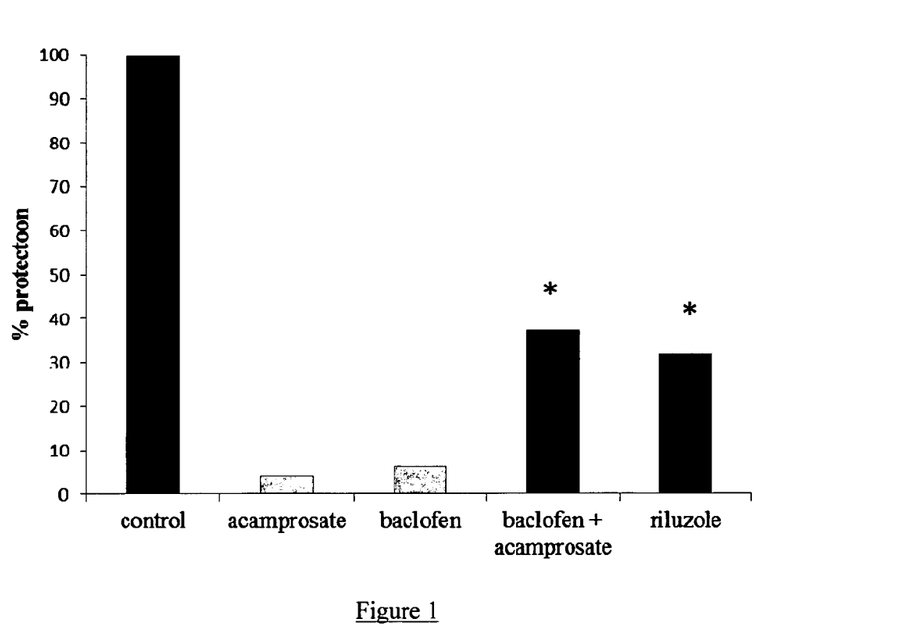
FIG. 1: Protective effect of Baclofen and Acamprosate combination therapy against ischemic injury. Whereas no significant protection is obtained when Baclofen (80 nM) or Acamprosate (0.32 nM) are used alone, a significant protection (*) is observed for the combination of the two drugs, at the same concentrations.
Figure 2:
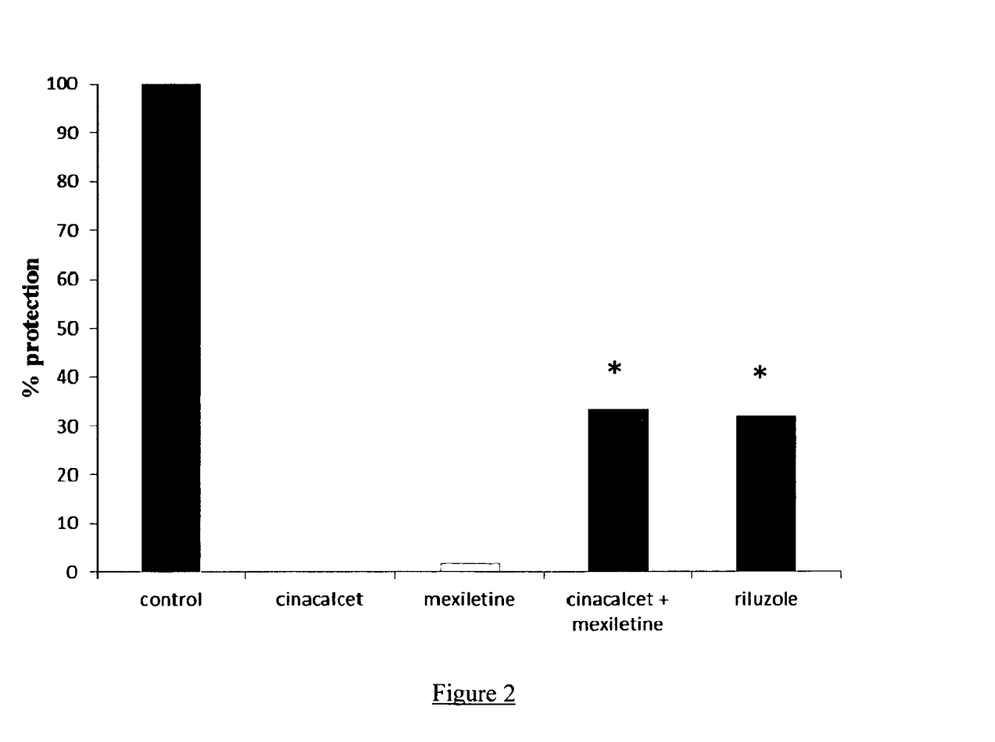
FIG. 2: Protective effect of Cinacalcet and Mexiletine combination therapy against ischemic injury. No significant protection is observed when Cinacalcet (64 pM) or Mexiletine (25.6 pM) are used alone, whereas a significant protection (*) is observed for the combination of the two drugs, at the same concentrations.
Figure 3:
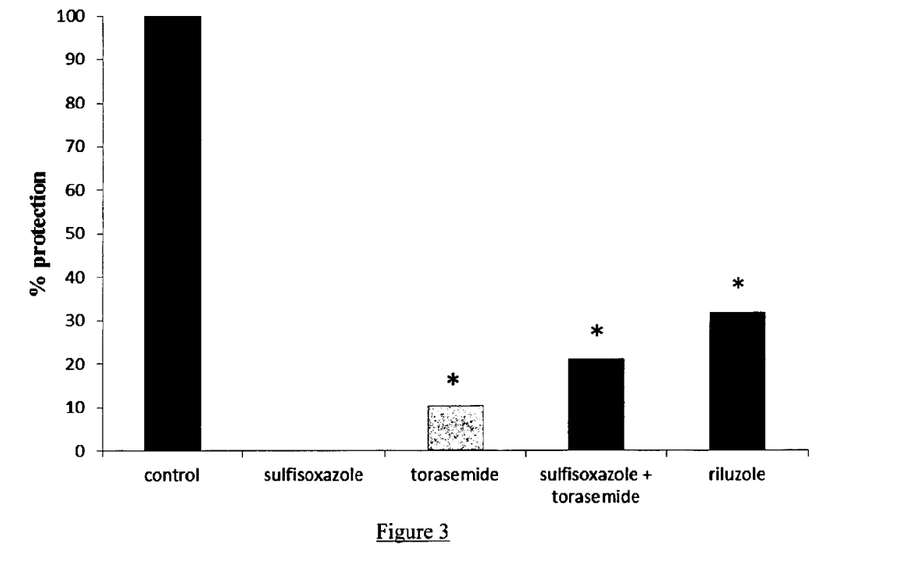
FIG. 3: Protective effect of Torasemide and Sulfisoxazole combination therapy against ischemic injury. The combination of Sulfisoxazole (1.36 nM) and Torasemide (80 nM) induce a significant protection (*), 110% higher than the protection obtained using Torasemide alone, whereas no protection is obtained when Sulfisoxazole is used alone.

FIGS. 1 to 3 further show that the combination treatments of the invention strongly protect neurons from oxygen and glucose deprivation.

As shown in FIGS. 1-3, effective protection is observed using drug concentrations at which the drugs, alone, have no significant protective effect. For example, a significant protective effect of Baclofen (80 nM)/Acamprosate (0.32 nM) combination, Cinacalcet (64 pM)/Mexiletine (25.6 pM) combination or Torasemide (80 nM)/Sulfisoxazole (1.36 nM) combination in ischemia is observed, while no significant protection is obtained when Baclofen, Acamprosate, Cinacalcet, Mexiletine and Sulfisoxazole are used alone at the same concentrations.

These results therefore demonstrate a potent and synergistic effect of the claimed combination therapies on brain ischemia and hypoxia.

Example 2: Protective Effect of Combination Treatments of the Invention Against Glutamate Toxicity Glutamate toxicity is often described in the literature as being a part of the ischemic cascade that leads to neuronal cell death. Combination therapies have been tested for their protective effect against glutamate toxicity in vitro.

Methods

Rat neuronal cortical cells are prepared as in Example 1 section.

Glutamate Toxicity Assays

The neuroprotective effect of compounds is assessed by quantification of the neurite network (Neurofilament immunostaining (NF)) which specifically reveals the glutamatergic neurons.

After 12 days of neuron culture, drugs of the candidate combinations are dissolved in culture medium (+0.1% DMSO). Candidate combinations are then pre-incubated with neurons for 1 hour before the glutamate injury. One hour after incubation, glutamate is added for 20 min, to a final concentration of 40 µM, in the presence of candidate combinations, in order to avoid further drug dilutions. At the end of the incubation, the medium is changed with medium with candidate combination but without glutamate. The culture is fixed 24 hours after glutamate injury. MK801 (20 µM) is used as a positive control.

After permeabilization with saponin (Sigma), cells are blocked for 2 h with PBS containing 10% goat serum, then the cells are incubated with mouse monoclonal primary antibody against Neurofilament antibody (NF, Sigma). This antibody is revealed with Alexa Fluor 488 goat anti-mouse IgG (Molecular probe).

Nuclei of cells are labeled by a fluorescent marker (Hoechst solution, SIGMA), and the neurite network is quantified. Six wells per condition are used to assess neuronal survival in 3 different cultures.

Results

The results are shown in Table 3 below. They show that all of the claimed drug combinations give a protective effect against glutamate toxicity for cortical neuronal cells.

TABLE 3

| Drug Combination | Neuroprotective effect against glutamate toxicity |
|---|---|
| Baclofen-Acamprosate | + |
| Baclofen-Torasemide | + |
| Baclofen-Homotaurine | + |
| Baclofen-Acamprosate-Torasemide | + |
| Mexiletine and Cinacalcet | + |
| Sulfisoxazole and Torasemide | + |

Figure 4:
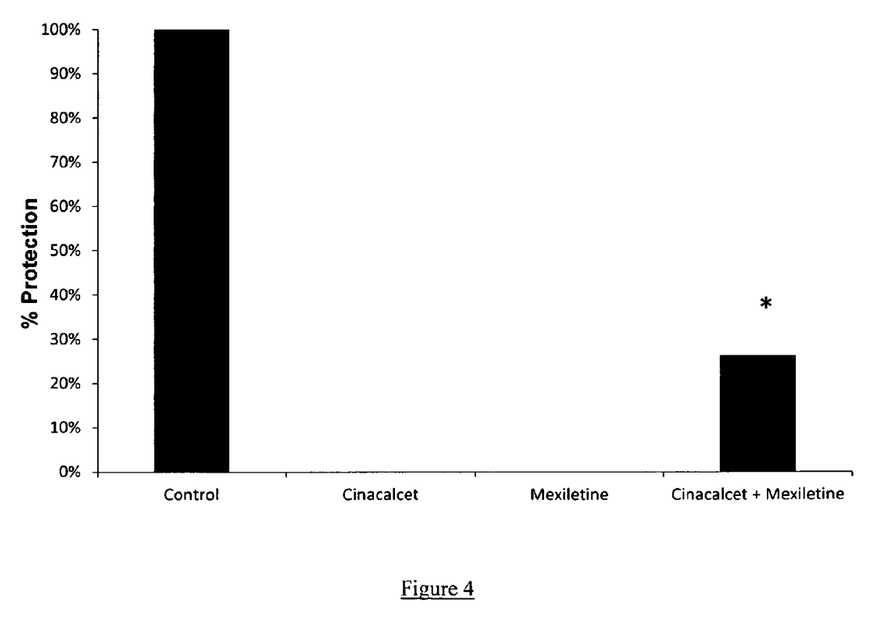
FIG. 4: Effect of Cinacalcet and Mexiletine combination therapy against glutamate toxicity on neuronal cortical cells. Glutamate intoxication is significantly prevented by the combination of Cinacalcet (64 pM) and Mexiletine (25.6 pM) whereas, at those concentrations, Cinacalcet and Mexiletine alone have no significant effect on intoxication. *: $p<0.001$, significantly different from glutamate intoxication (ANOVA+Dunnett Post-Hoc test).
Figure 5:
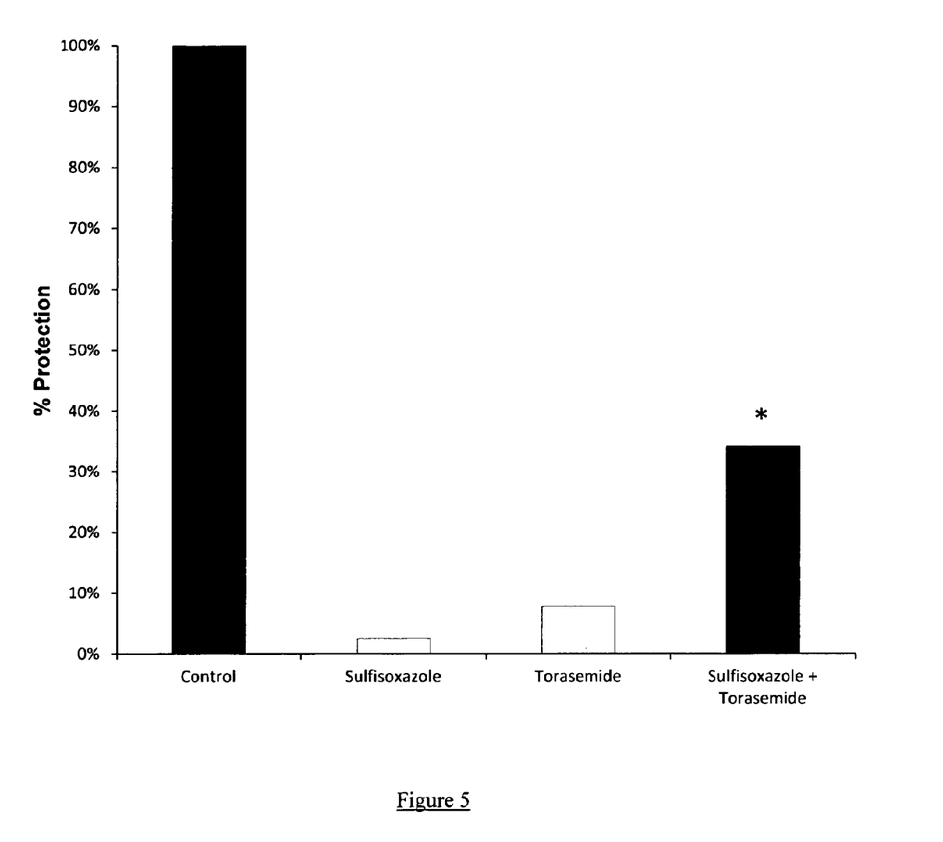
FIG. 5: Effect of Sulfisoxazole and Torasemide combination therapy against glutamate toxicity on neuronal cortical cells. Glutamate intoxication is significantly prevented by the combination of Sulfisoxazole (6.8 nM) and Torasemide (400 nM) whereas, at those concentrations, Sulfisoxazole and Torasemide alone have no significant effect on intoxication. *: $p<0.001$, significantly different from glutamate intoxication (ANOVA+Dunnett Post-Hoc test).

As exemplified in FIGS. 4 and 5, combinations of the invention strongly protect neurons from glutamate toxicity. The inventors have demonstrated that an effective protection is observed using concentrations at which the drugs alone have no significant effect. For instance, the glutamate intoxication is significantly prevented by the combination of Cinacalcet (64 pM)/Mexiletine (25.6 pM) or by the combination of Sulfisoxazole (6.8 nM)/Torasemide (400 nM), whereas, at the same concentrations, Cinacalcet, Mexiletine, Sulfisoxazole or Torasemide, used alone, have no significant effect on glutamate intoxication.

The above documented protection against glutamate toxicity together with the protection afforded under conditions of glucose and oxygen deprivation show that combination therapies of the invention are efficient in protecting neuronal cells under ischemic or hypoxic conditions.

REFERENCES

1. Roitberg, B., *Transplantation for stroke*. Neurological Research, 2004. 26(3): p. 256-264.
2. Armogida, M., et al., *The protective role of catalase against cerebral ischemia in vitro and in vivo*. Int J Immunopathol Pharmacol. 24(3): p. 735-47.
3. Ikonomidou, C. and L. Turski, *Why did NMDA receptor antagonists fail clinical trials for stroke and traumatic brain injury?* The Lancet Neurology, 2002. 1(6): p. 383-386.
4. Horn, J. and M. Limburg, *Calcium antagonists for acute ischemic stroke*. Cochrane Database Syst Rev, 2000(2): p. CD001928.
5. Cheng, Y. D., L. Al-Khoury, and J. A. Zivin, *Neuroprotection for ischemic stroke: two decades of success and failure*. NeuroRx, 2004. 1(1): p. 36-45.
6. Gribkoff, V. K., et al., *Targeting acute ischemic stroke with a calcium-sensitive opener of maxi-K potassium channels*. Nat Med, 2001. 7(4): p. 471-7.
7. Endres, M., et al., *Attenuation of delayed neuronal death after mild focal ischemia in mice by inhibition of the caspase family*. J Cereb Blood Flow Metab, 1998. 18(3): p. 238-47.
8. Ehrenreich, H., et al., *Recombinant human erythropoietin in the treatment of acute ischemic stroke*. Stroke, 2009. 40(12): p. e647-56.
9. Steffansen, B., et al., *Intestinal solute carriers: an overview of trends and strategies for improving oral drug absorption*. Eur J Pharm Sci, 2004. 21(1): p. 3-16.
10. Yang, C. Y., A. H. Dantzig, and C. Pidgeon, *Intestinal peptide transport systems and oral drug availability*. Pharm Res, 1999. 16(9): p. 1331-43.
11. Heimbach, T., et al., *Enzyme-mediated precipitation of parent drugs from their phosphate prodrugs*. International Journal of Pharmaceutics, 2003. 261(1-2): p. 81-92.
12. Beaumont, K., et al., *Design of ester prodrugs to enhance oral absorption of poorly permeable compounds: challenges to the discovery scientist*. Curr Drug Metab, 2003. 4(6): p. 461-85.
13. Ettmayer, P., et al., *Lessons Learned from Marketed and Investigational Prodrugs*. Journal of Medicinal Chemistry, 2004. 47(10): p. 2393-2404.
14. Stella, V. J., *Prodrugs: Challenges and Rewards*. 2007, New-York.
15. Wermuth, C., Chapter 33: *Designing prodrugs and bioprecursors*, in *The Practice of Medicinal Chemistry*. 2003.
16. Pezron, I., et al., *Prodrug strategies in nasal drug delivery*. Expert Opinion on Therapeutic Patents, 2002. 12(3): p. 331-340.
17. Stella, V. J., *Prodrugs as therapeutics*. Expert Opinion on Therapeutic Patents, 2004. 14(3): p. 277-280.
18. Stella, V. J. and K. W. Nti-Addae, *Prodrug strategies to overcome poor water solubility*. Adv Drug Deliv Rev, 2007. 59(7): p. 677-94.
19. Higuchi, T. S., V., *Prodrugs As Novel Drug Delivery Systems*. ACS Symposium Series. American Chemical Society. 1975, Washington D.C.
20. Roche, E. B., *Design of Biopharmaceutical Properties through Prodrugs and Analogs*. 1977: The Academy (Washington).
21. Lal, R., et al., *Arbaclofen placarbil, a novel R-baclofen prodrug: improved absorption, distribution, metabolism, and elimination properties compared with R-baclofen*. J Pharmacol Exp Ther, 2009. 330(3): p. 911-21.
22. Wishart, D. S., et al., *DrugBank: a knowledgebase for drugs, drug actions and drug targets*. Nucleic Acids Res, 2008. 36(Database issue): p. D901-6.
23. Johnston, S. C., et al., *Short-term prognosis after emergency department diagnosis of TIA*. JAMA, 2000. 284 (22): p. 2901-6.
24. Stahl H., Wermuth C. G. (Eds.) Handbook of *Pharmaceutical Salts*: Properties, Selection, and Use. Wiley-VCH; 2 edition (Mar. 29, 2011).
25. Wishart D S, Knox C, Guo A C, Cheng D, Shrivastava S, Tzur D, Gautam B, Hassanali M. *DrugBank: a knowledgebase for drugs, drug actions and drug targets*. Nucleic Acids Res. 36, Issuesuppl 1. D901-D906 (2008).
26. Hanafi R, Mosad S, Abouzid K, Niess R, Spahn-Langguth H. *Baclofen ester and carbamate prodrug candidates: a simultaneous chromatographic assay, resolution optimized with DryLab*. J Pharm Biomed Anal, 2011. 56(3): p. 569-76.
27. Singer C., Figueroa-Masot X., Batchelor R., and Dorsa D. *Mitogen-activated protein kinase pathway mediates estrogen neuroprotection after glutamate toxicity in primary cortical neurons*. J. Neuroscience, 1999. 19(7): 2455-2463.
28. Wang, Y. and Z. H. Qin, *Molecular and cellular mechanisms of excitotoxic neuronal death*. Apoptosis, 2010. 15(11): p. 1382-402.
29. Bano, D., et al., *The plasma membrane Na+/Ca2+ exchanger is cleaved by distinct protease families in neuronal cell death*. Ann NY Acad Sci, 2007. 1099: p. 451-5.
30. Crosby, N., K. H. Deane, and C. E. Clarke, *Amantadine in Parkinson's disease*. Cochrane Database Syst Rev, 2003(1): p. CD003468.
31. Andrew R. Leach, Valerie J. Gillet. An Introduction to Chemoinformatics. Springer 2007.
32. Syed A Rahman, Matthew Bashton, Gemma L Holliday, Rainer Schrader and Janet M Thornton, Small Molecule Subgraph Detector (SMSD) toolkit. Journal of Cheminformatics, 2009, 1:12.

The invention claimed is:

1. A method for the treatment of a brain ischemic or hypoxic injury in a subject in need thereof, comprising administering to said subject a combination of compounds selected from:
    baclofen at a dose between 0.01 and 150 mg per day and acamprosate at a dose between 1 and 2000 mg per day,
    baclofen at a dose between 0.01 and 150 mg per day and torasemide at a dose between 0.05 and 4 mg per day,
    baclofen at a dose between 0.01 and 150 mg per day and torasemide at a dose between 0.05 and 4 mg per day and acamprosate at a dose between 1 and 200 mg per day,
    mexiletine at a dose between 6 and 120 mg per day and cinacalcet at a dose between 0.3 and 36 mg per day, or
    sulfisoxazole at a dose between 20 and 800 mg per day and torasemide at a dose between 0.05 and 4 mg per day,
    or pharmaceutically acceptable salts, enantiomers, or racemates, said compounds in said combinations being in a synergistic amount.

2. The method according to claim 1, wherein said ischemic injury is a focal ischemic injury or a global ischemic injury.

3. The method according to claim 1, wherein said subject is suffering from or is susceptible to suffer from stroke, acute ischemic stroke, transient ischemic attack, acute hemorrhagic stroke, head trauma, brain hemorrhages, cardiac arrest, cerebral edema, hydrocephalus, asphyxia, thrombosis, embolism, thromboembolism, atherosclerosis, prolonged severe hypotension, intrauterine hypoxia, birth hypoxia, cardiac surgery complications or neurosurgery complications.

4. The method according to claim 1, to reduce, lessen or retard neuronal damage or neuronal cell death in a subject having ischemia or hypoxia.

5. The method according to claim 1, to protect a subject from brain ischemia or hypoxia.

6. The method according to claim 1, for treating brain ischemia or hypoxia, or for protecting neuronal cells, in a subject having suffered from, suffering from, or at risk to suffer from stroke.

7. The method according to claim 1, for protecting brain neuronal cells from ischemia or hypoxia, in a subject undergoing cardiac or neurosurgery.

8. The method according to claim 1, for treating brain ischemia or hypoxia, or for protecting neuronal cells, in a subject having suffered from a transient ischemic attack.

9. The method according to claim 1, for treating brain ischemia or hypoxia, or for protecting neuronal cells, in a subject at risk to suffer from reperfusion injury.

10. The method according to claim 1, wherein the compounds are admixed with a pharmaceutically acceptable carrier or excipient.

11. The method according to claim 1, wherein the compounds are formulated or administered together, separately or sequentially.

12. The method according to claim 1, wherein homotaurine is substituted for acamprosate.

13. The method according to claim 1, wherein said compounds are administered repeatedly to the subject.

14. The method according to claim 1, which comprises administering to said subject a combination of baclofen and acamprosate at a molar ratio baclofen/acamprosate from 10 to 400.

15. The method according to claim 1, which comprises administering to said subject a combination of baclofen and torasemide at a molar ratio baclofen/torasemide from 0.1 to 1000.

16. The method according to claim 1, which comprises administering to said subject a combination of mexiletine and cinacalcet at a molar ratio mexiletine:cinacalcet from 0.1 to 1000.

17. The method according to claim 1, which comprises administering to said subject a combination of sulfisoxazole and torasemide at a molar ratio sulfisoxazole:torasemide from 0.1 to 1000.

18. The method according to claim 12, wherein homotaurine is orally administered at a dose comprised between 1 and 20 mg per day.

* * * * *